(12) United States Patent
Tran et al.

(10) Patent No.: US 11,475,558 B2
(45) Date of Patent: Oct. 18, 2022

(54) ORGAN ISOLATION IN SCAN DATA

(71) Applicant: RAYTHEON COMPANY, Waltham, MA (US)

(72) Inventors: Tuan T. Tran, Plano, TX (US); Raymond Samaniego, Prosper, TX (US)

(73) Assignee: Raytheon Company, Waltham, MA (US)

( * ) Notice: Subject to any disclaimer, the term of this patent is extended or adjusted under 35 U.S.C. 154(b) by 316 days.

(21) Appl. No.: 16/683,159

(22) Filed: Nov. 13, 2019

(65) Prior Publication Data

US 2021/0142471 A1 May 13, 2021

(51) Int. Cl.
*G06T 7/00* (2017.01)
*G06T 7/136* (2017.01)
*G06T 7/11* (2017.01)
*G06T 7/174* (2017.01)
*G06F 17/16* (2006.01)
(Continued)

(52) U.S. Cl.
CPC ............ *G06T 7/0012* (2013.01); *G06F 17/16* (2013.01); *G06F 17/18* (2013.01); *G06T 5/30* (2013.01); *G06T 5/50* (2013.01); *G06T 7/11* (2017.01); *G06T 7/136* (2017.01); *G06T 7/174* (2017.01);
(Continued)

(58) Field of Classification Search
CPC ......... G16H 30/40; G06T 7/0012; G06T 7/11; G06T 7/174; G06T 5/30; G06T 7/136; G06T 5/50; G06T 2207/10081; G06T 2207/20212; G06T 2207/10088; G06F 17/16; G06F 17/18
See application file for complete search history.

(56) References Cited

U.S. PATENT DOCUMENTS 5,425,368 A 6/1995 Brandt
6,111,975 A 8/2000 Sacks et al.
(Continued)

FOREIGN PATENT DOCUMENTS

DE 10 2010 041 619 A1 3/2012
JP 2004-312434 A 11/2004
TW 201123076 A1 7/2011

OTHER PUBLICATIONS

Badakhshannoory, et al., "A Model-Based Validation Scheme for Organ Segmentation in CT Scan Volumes", IEEE Transactions on Biomedical Engineering, vol. 58, No. 9 Sep. 1, 2011 (pp. 2681-2693).
(Continued)

*Primary Examiner* — Yoshihisa Ishizuka
(74) *Attorney, Agent, or Firm* — Lewis Roca Rothgerber Christie LLP

(57) ABSTRACT

A method for analyzing scan data. In some embodiments, the method includes forming, from a first scan data array, a first mask, each element of the first mask being one or zero according to whether the corresponding element of the first scan data array exceeds a first threshold; forming, from the first scan data array, a second mask, each element of the second mask having a value of one or zero according to whether the corresponding element of the first scan data array exceeds a second threshold, the second threshold being less than the first threshold; and forming a fourth mask, the fourth mask being the element-wise product of the second mask and a third mask, the third mask being based on the first mask.

34 Claims, 2 Drawing Sheets

(51) Int. Cl.
  *G06F 17/18* (2006.01)
  *G06T 5/30* (2006.01)
  *G06T 5/50* (2006.01)
(52) U.S. Cl.
  CPC .............. *G06T 2207/10081* (2013.01); *G06T 2207/10088* (2013.01); *G06T 2207/20212* (2013.01)

(56) References Cited

U.S. PATENT DOCUMENTS

| | | | |
|---|---|---|---|
| 6,366,797 | B1 | 4/2002 | Fisher et al. |
| 6,760,611 | B1 | 7/2004 | Watanabe |
| 7,046,831 | B2 | 5/2006 | Ruchala et al. |
| 8,265,357 | B2 | 9/2012 | Ramsing et al. |
| 10,102,682 | B1 | 10/2018 | Samaniego et al. |
| 10,706,539 | B2 | 7/2020 | Samaniego et al. |
| 2002/0136439 | A1 | 9/2002 | Ruchala et al. |
| 2004/0102905 | A1 | 5/2004 | Adorjan et al. |
| 2005/0163358 | A1* | 7/2005 | Moeller .............. G06T 7/11 382/128 |
| 2005/0232474 | A1 | 10/2005 | Wei et al. |
| 2006/0171578 | A1* | 8/2006 | Novak .............. G06T 7/30 600/407 |
| 2006/0232608 | A1 | 10/2006 | Riaz |
| 2008/0026385 | A1 | 1/2008 | Sharma et al. |
| 2008/0049994 | A1* | 2/2008 | Rognin .............. G06T 7/35 382/128 |
| 2009/0129653 | A1 | 5/2009 | DeHority et al. |
| 2010/0246922 | A1 | 9/2010 | Uchihara et al. |
| 2011/0135173 | A1 | 6/2011 | Elbaroudi et al. |
| 2011/0150309 | A1 | 6/2011 | Barfett et al. |
| 2012/0038644 | A1 | 2/2012 | Jones et al. |
| 2012/0207270 | A1 | 8/2012 | Flohr et al. |
| 2012/0212598 | A1 | 8/2012 | Mowrey et al. |
| 2013/0051676 | A1 | 2/2013 | Wehnes et al. |
| 2014/0315732 | A1 | 10/2014 | Lobe |
| 2015/0004717 | A1 | 1/2015 | McDevitt et al. |
| 2015/0262359 | A1 | 9/2015 | Fujiwara et al. |
| 2015/0287188 | A1* | 10/2015 | Gazit .............. G06T 5/008 382/131 |
| 2015/0339809 | A1 | 11/2015 | Ohishi |
| 2016/0055632 | A1 | 2/2016 | Fu et al. |
| 2016/0080548 | A1 | 3/2016 | Erickson et al. |
| 2017/0071562 | A1 | 3/2017 | Suzuki |
| 2018/0278868 | A1 | 9/2018 | Dawson et al. |
| 2019/0076049 | A1* | 3/2019 | Satoh .............. A61B 5/055 |
| 2019/0172205 | A1 | 6/2019 | Mao et al. |
| 2020/0121219 | A1* | 4/2020 | Ganesan .............. A61B 90/11 |

OTHER PUBLICATIONS

International Search Report for corresponding International Application No. PCT/US2020/040319, filed Jun. 30, 2020, International Search Report dated Aug. 12, 2020 and dated Aug. 28, 2020 (5 pgs.).
Written Opinion of the International Searching Authority for corresponding International Application No. PCT/US2020/040219, filed Jun. 30, 2020, Written Opinion of the International Searching Authority dated Aug. 28, 2020 (10 pgs.).
Anonymous: "matlab—Extracting image region within boundary—Stack Overflow" retrieved from the Internet: URL:https://stackoverflow.com/questions/9442932/extracting-image-region-within-bounbdary, Mar. 2, 2012 (7 pgs.).
Anonymous: "Segmenting a cube in image by following the Coin segmentation tutorial. How to sort the blobs in a fixed order?—MATLAB Answers—MATLAB Central", retrieved from the Internet: URL:https://de.matworks.com/matlabcentral/answers/251547-segmenting-a-cube-in-image-by-following-the-coin-segmentation-tutorial-how-to-sort-the-blobs-in-a-f, Nov. 1, 2015 (8 pgs.).
Otsu N, "A Threshold Selection Method from Gray-Level Histograms", IEEE Transactions on Systems, Man and Cybernetics, IEEE Inc., vol. 9, No. 1, Jan. 1, 1979 (pp. 62-66).
Anonymous: "Region Growing problem with ginput—MATLAB Answers—MATLAB Central", retrieved from Internet: URL: https://de.mathworks.com/matlabcentral/answers/82743-region-growing-problem-with-ginput, Nov. 6, 2017 (7 pgs.).
Anonymous: "How can i segment a color image with region growing?—MATLAB Answers—MATLAB Central", retrieved from the Internet: URL: https://de.mathworks.com/matlabcentral/answers/53351-how-can-i-segment-a-color-image-with-region-growing, Nov. 2, 2017 (5 pgs.).
Storyblocks: "Photoshop Basics: How to Use the Magic Wand Tool", retrieved from the Internet: URL:https://www.youtube.com/watch?v?cwh4CbSFxIA [retrieved on Mar. 5, 2021] frames at instant 0:34, 0:40 and 0:42, Nov. 24, 2015 (2 pgs.).
International Search Report for related International Application No. PCT/US2020/052566, filed Sep. 24, 2020, International Search Report dated Mar. 5, 2021 and dated Mar. 16, 2021 (4 pgs.).
Written Opinion of the International Searching Authority for related International Application No. PCT/US2020/052566, filed Sep. 24, 2020, Written Opinion of the International Searching Authority dated Mar. 16, 2021 (6 pgs.).
Cai, Jinzheng et al., "Pancreas Segmentation in CT and MRI Images via Domain Specific Network Designing and Recurrent Neural Contextual Learning", Mar. 30, 2018, pp. 1-11, arXiv:1803.11303v1.
Cai, Jinzheng et al., "Pancreas Segmentation in MRI Using Graph-Based Decision Fusion on Convolutional Neural Networks", 2016, pp. 442-450, Springer International Publishing AG.
European Patent Office Communication pursuant to Rules 161(1) and 162 EPC, dated Nov. 26, 2019, for Patent Application No. EP18706015.7, 3 pages.
Fishman, Elliot K. et al., "Volume Rendering versus Maximum Intensity Projection in CT Angiography: What Works Best, When, and Why", RadioGraphics, May-Jun. 2006, pp. 905-922, vol. 26, No. 3, RSNA.
International Search Report and Written Opinion of the International Searching Authority, dated Apr. 24, 2018, corresponding to PCT/US2018/015693, 12 pages.
Kitano, S. et al., "Quantitative CT color mapping of the arterial enhancement fraction of the liver: A useful tool for the diagnosis of local hepatocellular carcinoma recurrences after TACE?", ECR, 2010, pp. 1-17, Poster No. C-0043, European Society of Radiology.
Mindek, Peter, "Maximum Intensity Projection Weighted by Statistical Cues", Proceedings of CESCG 2011, http://old.cescg.org/CESCG-2011/papers/TUBratislava-Mindek-Peter.pdf, retrieved Apr. 17, 2018, 7 pages.
Partial English translation of the Taiwanese Notice of Allowance, for Patent Application No. 107103473, dated Jul. 23, 2019, 1 page.
Persson, A. et al., "Standardized Volume Rendering for Magnetic Resonance Angiography Measurements in the Abdominal Aorta", Acta Radiologica, 2006, pp. 172-178, Taylor & Francis.
Taiwanese Notice of Allowance, for Patent Application No. 107103473, dated Jul. 23, 2019, 3 pages.
U.S. Appl. No. 16/537,384, filed Aug. 9, 2019, not yet published.
Zhu, Zhuotun et al., "Multi-Scale Coarse-to-Fine Segmentation for Screening Pancreatic Ductal Adenocarcinoma", Jul. 9, 2018, pp. 1-9, arXiv:1807.02941v1.
International Search Report for corresponding International Application No. PCT/US2018/046564, filed Aug. 13, 2018, International Search Report dated Oct. 18, 2018 and dated Oct. 25, 2018 (5 pgs.).
Kauanova, Sholpan et al., "Automated image segmentation for detecting cell spreading for metastasizing assessments of cancer development", Jan. 1, 2018.
Simon, Inpakala et al., "Automated Image Analysis System for Detecting Boundaries of Live Prostate Cancer Cells", Cytometry, 1998, pp. 287-294, Wiley-Liss, Inc.
Unpublished U.S. Appl. No. 16/740,186, filed Jan. 10, 2020.
Unpublished U.S. Appl. No. 17/116,878, filed Dec. 9, 2020.
Unpublished U.S. Appl. No. 17/116,964, filed Dec. 9, 2020.
Written Opinion of the International Searching Authority for corresponding International Application No. PCT/US2018/046564, filed Aug. 13, 2018, Written Opinion of the International Searching Authority dated Oct. 25, 2018 (9 pgs.).

(56) References Cited

OTHER PUBLICATIONS

Younes, R. Ben et al., "A fully automated contour detection algorithm the preliminary step for scatter and attenuation compensation in SPECT", European Journal of Nuclear Medicine, 1988, pp. 586-589, Springer-Verlag.

* cited by examiner

ORGAN ISOLATION IN SCAN DATA

CROSS-REFERENCE TO RELATED APPLICATION(S)

This application is related to and incorporates by reference in their entirety, as if set forth in full, U.S. patent application Ser. No. 16/537,384, filed Aug. 9, 2019, issued Jul. 13, 2021 as U.S. Pat. No. 11,062,512, entitled "SYSTEM AND METHOD FOR GENERATING 3D-COLOR REPRESENTATION OF 2D GRAY SCALE IMAGES", and U.S. Pat. No. 10,102,682, issued Oct. 16, 2018, entitled "SYSTEM AND METHOD FOR COMBINING 3D IMAGES IN COLOR".

FIELD

One or more aspects of embodiments according to the present invention relate to medical imaging, and more particularly to a system and method for isolating organs in medical imaging scans.

BACKGROUND

Medical imaging scans, such as magnetic resonance imaging (MRI) scans and computerized axial tomography (CT or CAT) scans are procedures that may be used to obtain information about the internal structure of an object, such as a patient. Medical imaging scans may be used to detect indications of cancer. Cancer in some organs, such as the pancreas, may be difficult to detect with a medical imaging scan because of the position of the organ within the body and the homogeneity of the surrounding tissue.

Finding an organ, such as the pancreas, in a medical imaging scan may be part of the process for assessing its health. The process of finding the organ may be time-consuming for a person, such as a radiologist, viewing the scan, and it may be difficult for the radiologist to reliably find the boundaries of the organ. Thus, there is need for a system and method for isolating organs in medical imaging scans.

SUMMARY

According to an embodiment of the present invention, there is provided a method for analyzing scan data, the method including: forming, from a first scan data array based on raw scan data, a first mask, each element of the first mask being one or zero according to whether the corresponding element of the first scan data array exceeds a first threshold; forming, from the first scan data array, a second mask, each element of the second mask having a value of one or zero according to whether the corresponding element of the first scan data array exceeds a second threshold, the second threshold being less than the first threshold; and forming a fourth mask, the fourth mask being the element-wise product of the second mask and a third mask, the third mask being based on the first mask.

In some embodiments: the third mask is a three dimensional array based on a fifth mask; the fifth mask is a three dimensional array based on the first mask, the forming of the third mask includes forming a slice of the third mask from a plurality of slices of the fifth mask, each element of the slice of the third mask having a value of: one, when any of the corresponding elements of the plurality of slices of the fifth mask has a value of one; and zero, otherwise.

In some embodiments, the fifth mask is based on a sixth mask, the sixth mask being based on the first mask, a slice of the fifth mask being formed by dilating the sixth mask.

In some embodiments, the method further includes forming the sixth mask based on a seventh mask, the seventh mask being based on the first mask, the forming of the sixth mask including setting to zero, in the sixth mask, one or more first connected regions, each of the first connected regions being an 8-connected region of ones, for which a measure of separation between a centroid of the first connected region and an estimated organ center exceeds a threshold distance.

In some embodiments, the measure of separation is a Chebyshev norm.

In some embodiments, the forming of the sixth mask further includes setting to zero one or more second connected regions, each of the second connected regions having an area exceeding an upper area threshold.

In some embodiments, the forming of the sixth mask further includes setting to zero one or more third connected regions, each of the third connected regions having an area less than a lower area threshold.

In some embodiments, the method further includes forming the first scan data array by multiplying a second scan data array by a cylindrical mask, the second scan data array being based on the raw scan data, each element of the cylindrical mask having a value of one if it is inside a cylindrical volume and a value of zero otherwise.

In some embodiments, the method further includes forming an eighth mask based on the fourth mask, the forming of the eighth mask including setting to zero, in the eighth mask, one or more fourth connected regions, each of the fourth connected regions being an 8-connected region of ones, for which: at least one corner of a square centered on the centroid of the connected region is at a location corresponding to a value of zero in the third mask, and a measure of separation between a centroid of the fourth connected region and an estimated organ center exceeds a threshold distance.

In some embodiments, the forming of the eighth mask further includes setting to zero one or more fifth connected regions, each of the fifth connected regions having an area exceeding an upper area threshold.

In some embodiments, the forming of the eighth mask further includes setting to zero one or more sixth connected regions, each of the sixth connected regions having an area less than a first lower area threshold.

In some embodiments, the forming of the eighth mask further includes: setting all elements of the eighth mask to zero, when a total number of ones in the eighth mask is below a second lower area threshold, and leaving the eighth mask unchanged, otherwise.

In some embodiments, the method further includes forming a ninth mask based on the eighth mask, the forming of the ninth mask including dilating a slice of a mask based on the eighth mask.

In some embodiments, the method further includes forming a tenth mask based on the ninth mask, the forming of the tenth mask including performing morphological closing on a slice of a mask based on the ninth mask.

In some embodiments, the method further includes projecting a third scan data array onto a plane to form a first image including a plurality of first pixel values at a plurality of pixel locations, the third scan data array being based on the raw scan data the projecting including: forming a vector for each pixel, the vector corresponding to array elements, of the third scan data array, along a line perpendicular to the plane and passing through the pixel location; calculating a plurality of statistics for each vector; and calculating the first pixel value for each vector as a weighted sum of the statistics of the plurality of statistics.

In some embodiments, the plurality of statistics includes two statistics selected from the group consisting of a vector mean, a vector maximum, and a vector standard deviation.

In some embodiments, the method further includes projecting a portion of the third scan data array onto a plane to form a second image including a plurality of first pixel values at a plurality of pixel locations, the projecting including: forming a vector for each pixel, the vector corresponding to array elements, of the portion of the third scan data array, along a line perpendicular to the plane and passing through the pixel location; calculating a plurality of statistics for each vector; and calculating the first pixel value for each vector as a weighted sum of the statistics of the plurality of statistics, the portion of the third scan data array being a plurality of consecutive slices of the third scan data array, the plurality of consecutive slices of the third scan data array including a maximum-valued slice, the maximum-valued slice being a slice containing the maximum value of the element-wise product of the third scan data array and the tenth mask.

In some embodiments, the method further includes forming a video including a first sequence of images, each of the first sequence of images being a different weighted sum of the first image and the second image.

In some embodiments, the method further includes forming a third image having: a first color component based on a first slice of a set of three slices of the element-wise product of the third scan data array and the tenth mask, the three slices including the maximum-value slice; a second color component based on a second slice of a set of three slices; and a third color component based on a third slice of a set of three slices.

In some embodiments, the video further includes a second sequence of images, each of the second sequence of images being a different weighted sum of the second image and the third image.

According to an embodiment of the present invention, there is provided a system including: a processing circuit, and a non-transitory memory, the non-transitory memory storing instructions that, when executed by the processing circuit, cause the processing circuit to: form, from a first scan data array based on raw scan data, a first mask, each element of the first mask being one or zero according to whether the corresponding element of the first scan data array exceeds a first threshold; form, from the first scan data array, a second mask, each element of the second mask having a value of one or zero according to whether the corresponding element of the first scan data array exceeds a second threshold, the second threshold being less than the first threshold; and form a fourth mask, the fourth mask being the element-wise product of the second mask and a third mask, the third mask being based on the first mask.

In some embodiments: the third mask is a three dimensional array based on a fifth mask; the fifth mask is a three dimensional array based on the first mask, the forming of the third mask includes forming a slice of the third mask from a plurality of slices of the fifth mask, each element of the slice of the third mask having a value of: one, when any of the corresponding elements of the plurality of slices of the fifth mask has a value of one; and zero, otherwise.

In some embodiments, the fifth mask is based on a sixth mask, the sixth mask being based on the first mask, a slice of the fifth mask being formed by dilating the sixth mask.

In some embodiments, the instructions further cause the processing circuit to form the sixth mask based on a seventh mask, the seventh mask being based on the first mask, the forming of the sixth mask including setting to zero, in the sixth mask, one or more first connected regions, each of the first connected regions being an 8-connected region of ones, for which a measure of separation between a centroid of the first connected region and an estimated organ center exceeds a threshold distance.

In some embodiments, the measure of separation is a Chebyshev norm.

In some embodiments, the forming of the sixth mask further includes setting to zero one or more second connected regions, each of the second connected regions having an area exceeding an upper area threshold.

In some embodiments, the forming of the sixth mask further includes setting to zero one or more third connected regions, each of the third connected regions having an area less than a lower area threshold.

In some embodiments, the instructions further cause the processing circuit to form an eighth mask based on the fourth mask, the forming of the eighth mask including setting to zero, in the eighth mask, one or more fourth connected regions, each of the fourth connected regions being an 8-connected region of ones, for which: at least one corner of a square centered on the centroid of the connected region is at a location corresponding to a value of zero in the third mask, and a measure of separation between a centroid of the fourth connected region and an estimated organ center exceeds a threshold distance.

In some embodiments, the instructions further cause the processing circuit to form a tenth mask based on the eighth mask, the forming of the tenth mask including performing morphological closing on a slice of a mask based on the eighth mask.

In some embodiments, the instructions further cause the processing circuit to project a third scan data array onto a plane to form a first image including a plurality of first pixel values at a plurality of pixel locations, the third scan data array being based on the raw scan data the projecting including: forming a vector for each pixel, the vector corresponding to array elements, of the third scan data array, along a line perpendicular to the plane and passing through the pixel location; calculating a plurality of statistics for each vector; and calculating the first pixel value for each vector as a weighted sum of the statistics of the plurality of statistics.

According to an embodiment of the present invention, there is provided a system for generating a view of an interior of an object, the system including: a scanner for scanning the object; a processing circuit; and a display, the processing circuit being configured to: form, from a first scan data array based on raw scan data, a first mask, each element of the first mask being one or zero according to whether the corresponding element of the first scan data array exceeds a first threshold; form, from the first scan data array, a second mask, each element of the second mask having a value of one or zero according to whether the corresponding element of the first scan data array exceeds a second threshold, the second threshold being less than the first threshold; and form a fourth mask, the fourth mask being the element-wise product of the second mask and a third mask, the third mask being based on the first mask.

In some embodiments: the third mask is a three dimensional array based on a fifth mask; the fifth mask is a three dimensional array based on the first mask, the forming of the third mask includes forming a slice of the third mask from a plurality of slices of the fifth mask, each element of the slice of the third mask having a value of: one, when any of the corresponding elements of the plurality of slices of the fifth mask has a value of one; and zero, otherwise.

In some embodiments, the fifth mask is based on a sixth mask, the sixth mask being based on the first mask, a slice of the fifth mask being formed by dilating the sixth mask.

In some embodiments, the processing circuit is further configured to form the sixth mask based on a seventh mask, the seventh mask being based on the first mask, the forming of the sixth mask including setting to zero, in the sixth mask, one or more first connected regions, each of the first connected regions being an 8-connected region of ones, for which a measure of separation between a centroid of the first connected region and an estimated organ center exceeds a threshold distance.

In some embodiments, the measure of separation is a Chebyshev norm.

In some embodiments, the forming of the sixth mask further includes setting to zero one or more second connected regions, each of the second connected regions having an area exceeding an upper area threshold.

In some embodiments, the forming of the sixth mask further includes setting to zero one or more third connected regions, each of the third connected regions having an area less than a lower area threshold.

In some embodiments, the processing circuit is further configured to form an eighth mask based on the fourth mask, the forming of the eighth mask including setting to zero, in the eighth mask, one or more fourth connected regions, each of the fourth connected regions being an 8-connected region of ones, for which: at least one corner of a square centered on the centroid of the connected region is at a location corresponding to a value of zero in the third mask, and a measure of separation between a centroid of the fourth connected region and an estimated organ center exceeds a threshold distance.

In some embodiments, the processing circuit is further configured to form a tenth mask based on the eighth mask, the forming of the tenth mask including performing morphological closing on a slice of a mask based on the eighth mask.

In some embodiments, the processing circuit is further configured to project a third scan data array onto a plane to form a first image including a plurality of first pixel values at a plurality of pixel locations, the third scan data array being based on the raw scan data the projecting including: forming a vector for each pixel, the vector corresponding to array elements, of the third scan data array, along a line perpendicular to the plane and passing through the pixel location; calculating a plurality of statistics for each vector; and calculating the first pixel value for each vector as a weighted sum of the statistics of the plurality of statistics.

BRIEF DESCRIPTION OF THE DRAWINGS

Features, aspects, and embodiments are described in conjunction with the attached drawings, in which.

DETAILED DESCRIPTION

Figure 1:
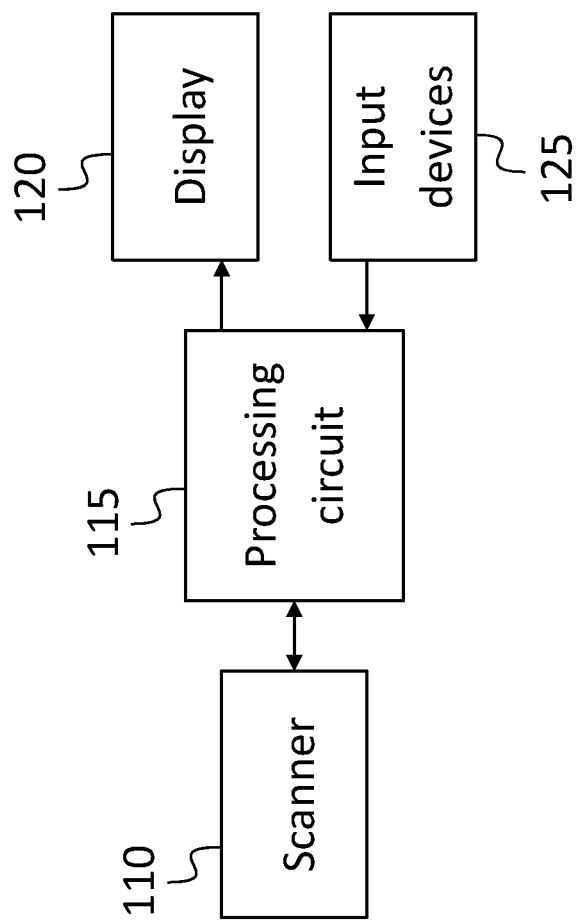
FIG. 1 is a system for generating images of the interior of an object, according to an embodiment of the present invention.

The detailed description set forth below in connection with the appended drawings is intended as a description of exemplary embodiments of a system and method for isolating organs in medical imaging scans provided in accordance with the present invention and is not intended to represent the only forms in which the present invention may be constructed or utilized. The description sets forth the features of the present invention in connection with the illustrated embodiments. It is to be understood, however, that the same or equivalent functions and structures may be accomplished by different embodiments that are also intended to be encompassed within the scope of the invention. As denoted elsewhere herein, like element numbers are intended to indicate like elements or features.

A computerized axial tomography (CAT) scan is a procedure in which an object (e.g., a patient) is illuminated from several directions with penetrating (e.g., X-ray) radiation from a radiation source, and a scan image of the transmitted radiation is formed, in each instance, by a detector, to form a plurality of scan images, each of which may be represented as a two-dimensional array. The radiation may be attenuated at different rates in different kinds of matter; accordingly, each point in each image may correspond to a transmitted radiant intensity depending on the attenuation rates of the compositions of matter on the path along which the radiation traveled from the radiation source to the detector. From the combination of scan images, raw scan data, e.g., a three-dimensional model of the "density" of the object may be formed. As used herein, the "density" within an object is any characteristic that varies within the object and that is measured by the medical imaging scan. For example, with respect to CAT scans, the "density" may refer to the local rate of attenuation of the penetrating radiation and with respect to MRI scans, the "density" may refer to the density of atoms having a nuclear resonance at the frequency of the probe radio frequency signal, in the presence of the magnetic field being applied. Although some examples are discussed in the present disclosure in the context of CAT scans or MRI scans of a human patient, the invention is not limited thereto, and in some embodiments other kinds of scans providing three-dimensional density data such as magnetic resonance imaging scans or positron emission tomography scans, or scans of objects other than human patients may be processed in an analogous fashion. In the case of other kinds of scans, density may be defined accordingly; in the case of a positron emission tomography scan, for example, the density may be the density of nuclei that decay by beta plus emission. As used herein, the term "object" includes anything that may be scanned, and encompasses without limitation human patients, animals, plants, inanimate objects, and combinations thereof.

When the object being imaged is a human patient (or other living object), a contrast agent may be used (e.g., injected into or ingested by the patient) to selectively alter the density of some tissues. The contrast agent may for example include a relatively opaque substance (i.e., relatively opaque to the penetrating radiation). The density of tissue containing the contrast agent may be increased as a result, and it may be increased to an extent that depends on the concentration of contrast agent in the tissue.

FIG. 1 shows a block diagram of a system for performing a scan and processing and displaying the results, according to one embodiment. The system includes a scanner 110, a processing circuit 115 (described in further detail below), a display 120 for displaying images, or sequences of images in the form of a movie (or "video"), and one or more input devices 125 such as a keyboard or mouse, that an operator (e.g., a radiologist) may use to operate the system, and to set parameters affecting the processing of the images to be displayed. It should be noted that the processing circuit 115, the display 120, and the input devices 125 may be part of a unitary system or may be a distributed system with the processing circuit 115, for example, being separate and communicatively coupled to the display 120 and input devices 125. In some embodiments, servers store the images and clients call the images, with image processing performed on the server or on the client, or both.

A plurality of scans may be performed, and analyzed together. For example, a first scan of an object (e.g., a patient) may be performed before the contrast agent is injected, and several subsequent scans of the object may be performed at various times (e.g., at regular intervals) after injection of the contrast agent, as the concentration of contrast agent changes. The rate at which the concentration of contrast agent increases initially, the peak concentration reached, and the rate at which the concentration of contrast agent subsequently decreases all may depend on the type of tissue into which the contrast is injected or which is of interest.

In some embodiments, various methods may be employed to generate images from medical imaging scan data to aid in the use of a medical imaging scan as a diagnostic tool. A sequence of steps, or "acts" illustrated in FIG. 2 and discussed in further detail below may be used, for example, to isolate an organ of interest (e.g., an organ suspected of having a tumor) and to form a video or series of images in which the isolated organ of interest is more readily apparent than in the raw scan data.

In some embodiments, arrays containing the three-dimensional scan data are received (from the scanner 110, via a portion of the processing circuit 115 that converts raw scan images to raw density arrays, or via processes, executed in the processing circuit 115, that perform this conversion), in a step 205. A cylindrical mask is applied (for one slice at a time of the three-dimensional scan data array) in a step 210; the result of the step 210 is a masked scan data array. The output of step 210 is converted to a binary mask in step 215, by comparing each element to a first threshold, and (i) setting the corresponding element of the mask to one if the element of the scan data array exceeds the first threshold, and (ii) setting it to zero otherwise. Additional processing is then performed, at 220, as discussed in further detail below, and as set forth, for example, in Listing 1. Such additional processing may include, for example, removing from the mask regions that are too small or too large, or too far from an estimated organ center. The estimated organ center may be a point in the scan data array selected based on the typical location of the organ of interest in the patient and the typical location of the patient in or on the scanner. The additional processing may also include dilating a mask to form a dilated mask.

Several consecutive slices of the mask (stored, in the code of Listing 1, in the variable maskIM) produced by the step 220 may then be combined in step 225 to form a combined mask (stored, in the code of Listing 2, in the variable combMask1). The forming of combMask1 may include forming a slice of the combined mask from several consecutive slices of maskIM, each element of the slice of combMask1 having (i) a value of one, when any of the corresponding elements of the several consecutive slices of maskIM has a value of one, and (ii) a value of zero, otherwise.

At 230, the output of step 210 is also converted to a binary mask in step 230, by comparing each element to a second threshold, and (i) setting the corresponding element of the mask to one if the element of the scan data array exceeds the second threshold, and (ii) setting it to zero otherwise. At 235, this mask is multiplied by combMask1, which is the output of step 225, and, at 240, the product is further processed (as described in further detail below), to form an updated mask, again stored in the variable maskIM. Various images may then be formed (as discussed in further detail below) at 245 (using statistics taken along the z-direction), at 250 (forming a color image from several grayscale slices), and at 255 (multiplying an image—e.g., the color image produced at step 250—by the mask maskIM); these images may be merged into a video at 260. The images formed at 245-255 and the video formed at 260 may have the characteristic that the organ of interest is more readily perceptible in these images than in the raw scan data.

Figure 2:
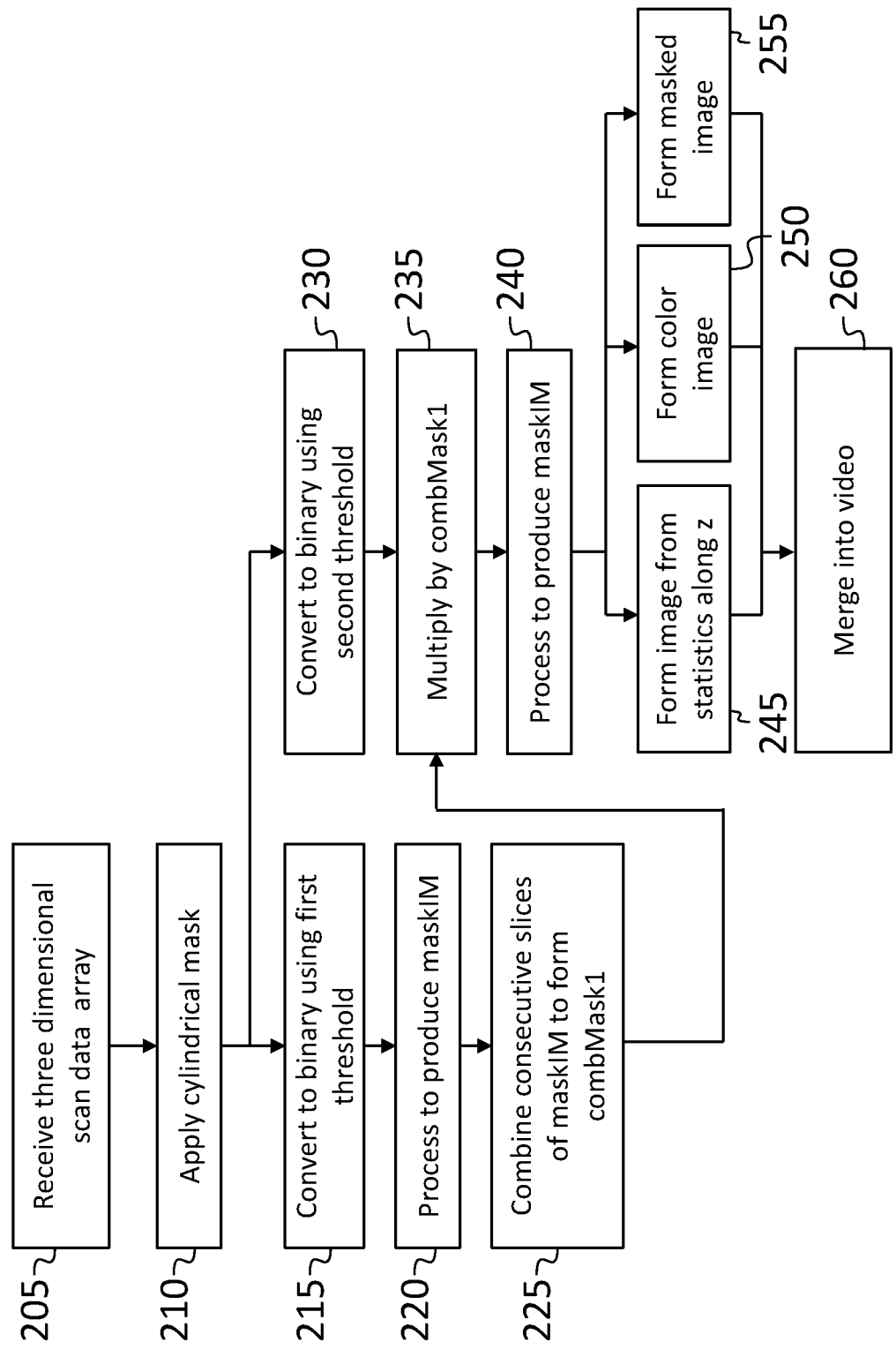
FIG. 2 is a flow chart of a method for generating images or video of the interior of an object, according to an embodiment of the present invention.

The steps of FIG. 2 can be further understood via the code listed in Listing 1, which shows MATLAB™ code for producing images and video in which an organ of interest (e.g., the pancreas) may be more readily perceptible than in the raw scan data. In step 205, and on line 19 of Listing 1, a data file is read in; in this example, the file contains raw scan data, in an array named MRI. This raw scan data is assigned, on line 26 of Listing 1, to the array dataIM. Lines 43-64 of Listing 1 assign parameter values used in subsequent lines of Listing 1 and Listing 2. At lines 101-108 of Listing 1, the threshold BW_Thrsh (used at line 145 of Listing 1, as discussed in further detail below) may be adjusted to have a linearly varying component; this feature may be employed to improve the visibility of a portion of an organ (e.g., the tail of the pancreas) that may have lower density than the remainder of the organ.

The array dataIM is processed, one slice at a time, in a loop spanning lines 135-218 of Listing 1. As used herein, a "slice" is a two-dimensional array. A slice of a three-dimensional array is a two-dimensional sub-array of the three-dimensional array, in a plane perpendicular to one of the three dimensions. As used herein, a slice of a two-dimensional array is the two-dimensional array.

At line 136 of Listing 1 the current slice of dataIM is assigned to the two-dimensional array f. In step 210, and at line 142 of Listing 1, f is multiplied by a mask, mask0, that is defined, on line 116 of Listing 1, as a circular disk of ones, the remainder of the mask being zeros. In three dimensions, this has the effect of masking the raw scan data array so that only a cylindrical region, that is expected to include the organ of interest, remains (i.e., is not set to zero). The result of the masking operation, for the current slice, is the slice f2. As used herein, (two or three dimensional) arrays that contain binary values (such as mask0) may be referred to as "masks" or "mask arrays", and (two or three dimensional) arrays that contain non-binary scan data or processed scan data may be referred to as "scan data arrays". As such, a masked scan data array (i.e., the element-wise product of a mask and a scan data array) is a scan data array.

In step 215, and at line 145 of Listing 1, the slice f2 is converted to a corresponding slice of a binary mask (or "first mask" BW), each element of the binary mask being one or zero according to whether the corresponding element of the scan data array f2 exceeds a first threshold. When an element of f2 exceeds the threshold, the corresponding element of the mask BW is set to one; otherwise, it is set to zero. The threshold is BW_Thrsh, scaled to maxVal; BW_Thrsh is assigned at line 108 or 110 of Listing 1, BW_percentThrs (used in these assignments) is assigned at line 59 of Listing 1, and BinThrs_1 is assigned at line 48 of Listing 1.

In step 220, and on lines 148-186 of Listing 1, the initial binary mask BW is further processed to produce a mask maskIM (a "fifth mask") (formed one slice at a time in the two-dimensional mask mask3). At line 148 of Listing 1, small connected regions are removed using the MATLAB™ bwareaopen( ) function, and the result is assigned, at lines 148 and 150 of Listing 1, to BW2 (a "seventh mask") and then to mask2 (a "sixth mask"). The call to bwareaopen( ) may have the effect of removing a significant number of small noise-like connected regions. Each connected region removed in this manner is an 8-connected region of ones containing fewer than removeSmallObjPixel ones (where the value of removeSmallObjPixel is set on line 60 of Listing 1). These connected regions are referred to as "blobs" in the comments in Listing 1 and in Listing 2.

The connected regions of mask2 are analyzed using calls to the MATLAB™ regionprops( ) function, at lines 152-154 of Listing 1. In lines 164-174 of Listing 1, any connected region having (i) a centroid too distant from an estimated organ center, (ii) an area that is too small, or (iii) an area that is too large is set to zero in mask2. In particular, in line 166 of Listing 1 the variable inPan is set to zero if the Chebyshev norm (the maximum of (i) the x component and (ii) the y component) of the vector from the centroid of the connected region to the estimated organ center exceeds a threshold (cenErrThrs), and in lines 167 and 172 of Listing 1, elements of mask2 for which (i) inPan is set to zero, or (ii) the area of the connected region is less than areaMin, or (iii) the area of the connected region is greater than areaMax are set to zero.

On line 186 of Listing 1, a mask, mask3, is formed by dilating mask2 using the MATLAB™ imdilate( ) function. This function inserts, in mask3, a disk of ones having a radius of 3 (diskfilter, defined on line 61 of Listing 1) for each element with a value of one in mask2. The three-dimensional mask maskIM is then formed, at line 200 of Listing 1, from the different values assigned to the slice mask3 over the set of iterations of the loop spanning lines 135-218 of Listing 1.

The code of Listing 2 uses the mask array maskIM and the corresponding array of slice areas sliceArea to generate a new three-dimensional mask (also stored in the variable maskIM) that may have ones in elements corresponding to the organ of interest, and zeros elsewhere. This three-dimensional mask may then be used (as, for example, in the code of Listing 3) to create images or videos in which the organ of interest is more readily perceptible than in the raw scan data.

In line 7 of Listing 2, a slice that is in the middle of the slices, of maskIM, having an area greater than 90% of the maximum area is identified. A range of slices of interest sliceIndx2 is then defined, on line 31 of Listing 2. In a loop spanning lines 35-156 of Listing 2, the slices of dataIM corresponding to the range sliceIndx2 is processed, to form the new mask which is then stored in the variable maskIM.

In step 225, and at lines 37-41 of Listing 2, a mask, combMask1 (a "third mask"), is formed from a plurality of slices of maskIM. Each element of combMask1 has (i) a value of one when any of the corresponding elements of the plurality of slices of the fifth mask has a value of one; and (ii) a value of zero, otherwise. On line 43 of Listing 2, the current slice of dataIM is copied into f, and at line 59 of Listing 2, f is multiplied by a mask, mask0, that is defined, on line 116 of Listing 1, as a circular disk of ones, the remainder of the mask being zeros. The result of the masking operation is the slice f2.

In step 230, and at line 62 of Listing 2, the slice is converted to a corresponding slice of a binary mask BW (a "second mask"), in which each value of f2 is compared to a second threshold, which is based on BinThrs_2, defined on line 89 of Listing 1, and which is lower than the first threshold used on line 145 of Listing 1. When an element of f2 exceeds the threshold, the corresponding element of the mask BW is set to one; otherwise it is set to zero.

At line 64 of Listing 2 small connected regions are removed using the MATLAB™ bwareaopen( ) function, and the result is assigned to BW2. In step 235, and at line 66 of Listing 2, BW2 is masked with combMask1 (an element-wise product of BW2 and combMask1 is formed), and the result is assigned to mask2 (a "fourth mask").

In step 240, and on lines 69-138 the binary mask mask2 is further processed to produce a mask maskIM (formed one slice at a time in the two-dimensional mask mask4).

The connected regions of mask2 are analyzed using calls to the MATLAB™ regionprops( ) function, at lines 69-71 of Listing 2.

In lines 90-107 of Listing 2, any connected region that (i) fails a subcentroid test and has a centroid too distant from an estimated organ center, or (ii) has an area that is too small, or (iii) has an area that is too large, is set to zero in mask2. The results of the subcentroid test are calculated at lines 90-94 of Listing 2; any connected region for which at least one corner of a square centered on the centroid of the connected region is at a location corresponding to a value of zero in combMask1 fails this test. The centroid test is failed, on line 95 of Listing 2, if the Chebyshev norm (the maximum of (i) the x component and (ii) the y component) of the vector from the centroid of the connected region to the estimated organ center exceeds a threshold (cenErrThrs). In lines 101 and 106 of Listing 2, elements of mask2 for which (i) inPan is set to zero (i.e., which failed both the subcentroid test and the centroid test) or (ii) the area of the connected region is less than areaMin or (iii) the area of the connected region is greater than areaMax are set to zero. At lines 111-115 mask2 is set entirely to zero if the total area (the total number of ones in the mask) is less than 2*areaMin (and left unchanged otherwise) (forming an "eighth mask").

At line 119 of Listing 2, a mask, mask3 (a "ninth mask"), is formed by dilating mask2 using the MATLAB™ imdilate( ) function. At lines 125-137 of Listing 2, if the current mask slice, mask3, contains more than one connected region, morphological closing is performed (to form a "tenth mask"), using a call, on line 127 of Listing 2, to the MATLAB™ imclose( ) function. The imclose( ) function may have the effect of performing a dilation followed by an erosion. Either (i) the result of the morphological closing of mask3, or (ii) mask3 itself, if there is only one connected region in mask3, is assigned to mask4. The three-dimensional mask maskIM is then formed, at line 138 of Listing 2, from the different values assigned to the slice mask3 over the set of iterations of the loop spanning lines 35-156 of Listing 2.

Steps 245-260 can be further understood via Listing 3, which is a listing of code that is used to display images or video in which the organ of interest is more readily perceptible than in the raw scan data. The code of Listing 3 uses, as an exemplary file, a CT scan; similar or identical code may be used to display data from another type of scan, e.g., an MRI scan, in an analogous manner. The mask, which defines the volume containing the organ of interest, is read in at line 14 of Listing 3, and assigned, at line 15 of Listing 3, to CT_ARmask. The slice containing the maximum value (e.g., the maximum density) in the masked scan is found at line 24 of Listing 3 and its index is assigned to zmax. At line 41 of Listing 3, an image, im0, is formed as a weighted sum (each weight being 1) of three statistics per pixel of the image, each of the statistics being taken over a vertical vector (a vector parallel to the z-axis) in the three-dimensional scan data array, the three statistics being the maximum value, the mean, and the standard deviation. This image im0 is displayed on lines 42 and 43 of Listing 3, and made into the first frame of a video at line 47.

At lines 49-52 of Listing 3, frames 2-30 of the video are set to be duplicates of the first frame. A second image is formed at line 54 of Listing 3. This image contains, in each pixel, the maximum value of the three corresponding pixels in the three consecutive slices, of the three-dimensional scan data array, centered on the slice at zmax. Because these slices are centered on the slice containing the maximum value (e.g., the maximum density) in the masked scan (and because the mask is constructed to contain the organ of interest), in this image the organ of interest may be more readily perceptible than in the raw scan data.

At lines 61-67 of Listing 3, 30 additional frames are added to the video, each containing a weighted average of the first and second images, with the relative weights changing linearly over the set of frames, the effect being a gradual fading from the first image im0 to the second image im1.

At lines 71-84 of Listing 3, a color image Mov2 is constructed from three consecutive slices of the three-dimensional scan data array, each color component (of red, green, and blue) being supplied by a respective one of the three consecutive slices. At lines 87-99, 30 additional frames are added to the video, each containing a weighted average of the second image im1 and the color image Mov2, with the relative weights changing linearly over the set of frames, the effect being a gradual fading from the second image im1 to the color image Mov2.

At lines 103-149 of Listing 3, another 15 frames are added, each containing a weighted average of (i) the color image Mov2 and (ii) the product of the mask maskIM with the color image Mov2, with the relative weights changing linearly over the set of frames, the effect being a gradual fading out of the portions of the image that are zero in the mask.

Listing 4 shows code for forming a color image from a masked scan array (e.g., a masked CT scan array). The masked scan array may be formed by multiplying scan data (e.g., density data) by a mask (or "segmentation mask", e.g., a mask that has ones in a volume corresponding to an organ of interest, and zeros elsewhere). In Listing 4, k may be the center slice of the segmentation mask for the organ of interest. Line 1 of Listing 4 defines an index identifying a slice corresponding to each of a red component, a green component, and a blue component of a color image the three color components of which are defined on lines 2-4 of Listing 4. The code of listing 4 may be used when the organ of interest extends only within, or is largely contained within, three slices of the scan.

The code of Listing 5 may be used when the organ of interest extends only within, or is largely contained within, twelve slices of the scan (or with minor modifications, nine slices, or fifteen slices, or a number of slices that is a larger multiple of three). In some embodiments, if the number of slices within which the organ extends is not a multiple of three (i.e., if the mask has non-zero elements in a number of slices that is not a multiple of three), the number of slices may be increased by one (by adding a slice at one end of the range), or by two (by adding a slice at each end of the range). The added slices may be ones for which the mask has only zeros, which may result in, for example, one or two of the color components of a resulting color image being somewhat less bright than they would be otherwise.

In the code of Listing 5, lines 2-4 define index ranges for red, green, and blue respectively. On lines 6-8, R is a subset of 4 consecutive slices of the masked scan array, G is another subset of 4 consecutive slices, and B is another subset of 4 consecutive slices. The red, green and blue components of a color image are then formed (in the arrays r, g, and b, respectively) as weighted sums of statistics (e.g., three statistics, the maximum, the mean, and the standard deviation, in the example of lines 10-12 of Listing 5), each statistic being calculated for a vector perpendicular to the slices, each vector corresponding to one of the pixels of the image which is formed, after sharpening (in lines 14-16 of Listing 5), at lines 18-22 of Listing 5.

Listing 1

```
1    % Raytheon Proprietary
2    close all
3    clear all
4    cd ('C:\data\Work\Apollo_MDA\2019\code')
5    addpath .\tool
6    dataType=1; % (1:MRI, 2:hgCT)
7    % 7/22/19 include import ("load mask2_1043") todo sub centroid
8    % 7/23/19 do 3D mask on pass 1 (with higher threshold to get boundary)
9    %        & do 2nd pass (lower threshold to get lower intensity)
10   %        expand\merge if mult part
11
12   %% Read in input data
13   %fileName =
       'C:\data\Work\Apollo_MDA\2019\data\data20190722\0556_MRI_WO.mat';%
       104slices of 512x384-->70?
14   %fileName =
       'C:\data\Work\Apollo_MDA\2019\data\data20190722\0622_MRI_WO.mat';%
       40slices of 256x192-->24?
15   %fileName =
       'C:\data\Work\Apollo_MDA\2019\data\data20190722\0770_MRI_WO.mat';%
       96slices of 320x240-->48?
16   %fileName =
       'C:\data\Work\Apollo_MDA\2019\data\data20190722\0779_MRI_WO.mat';%
       44slices of 256x176-->31? 22?
17   %fileName =
       'C:\data\Work\Apollo_MDA\2019\data\data20190722\0782_MRI_WO.mat';%
       68slices of 512x512-->38?¬?
```

-continued

| | Listing 1 |
|---|---|
| 18 | %fileName = 'C:\data\Work\Apollo_MDA\2019\data\data20190722\0802_MRI_WO.mat';% 51slices of 320x240%-->27 |
| 19 | fileName = 'C:\data\Work\Apollo_MDA\2019\data\data20190722\1031_MRI_WO.mat';% 44slices of 256x192%%%-->17 |
| 20 | %fileName = 'C:\data\Work\Apollo_MDA\2019\data\data20190722\1048_MRI_WO.mat';% 48slices 256x176%#-->34 |
| 21 | %fileName = 'C:\data\Work\Apollo_MDA\2019\data\data20190722\1224_MRI_WO.mat';% 47slices 320x260%%-->33 |
| 22 | %fileName = 'C:\data\Work\Apollo_MDA\2019\data\data20190722\1251_MRI_WO.mat';% 112slices 512x512-->52⁻? |
| 23 | |
| 24 | if ~isempty(fileName) |
| 25 |    load (fileName); |
| 26 |    dataIM= MRI; % MRI |
| 27 |    [row, col,numSlice,]=size(dataIM); % |
| 28 |    maskIM= zeros(row,col,numSlice); |
| 29 |    %maskSlim= zeros(row,col,numSlice); |
| 30 |    fileNameNum = char(fileName(end-14:end-11)); |
| 31 |    disp(['file name: ' fileNameNum]); |
| 32 | else |
| 33 |    fileName = 'C:\data\Work\Apollo_MDA\2019\data\highGrade\hgMRI.mat';% 26slices 384x512-->17 |
| 34 |    load (fileName); |
| 35 |    dataIM= HgMRI; % MRI |
| 36 |    [row, col,numSlice,]=size(dataIM); % |
| 37 |    maskIM= zeros(row,col,numSlice); |
| 38 |    %maskSlim= zeros(row,col,numSlice); |
| 39 |    fileNameNum = char(fileName(end-8:end-4)); |
| 40 |    disp(['file name: ' fileNameNum]); |
| 41 | end |
| 42 | |
| 43 | %% Inputs for process data |
| 44 |    saveMaskFlg =0; % flag to save mask todo movie or other |
| 45 |    flagWeiThrsh =0; % adj weight threshold to magnify the tail or head of pan |
| 46 | % use Binary thresh func of Max value |
| 47 | % or (edges(12) & edge(13) of [aa,edges]=histcounts(dataIM,30); |
| 48 |    BinThrs_1=0.38; %0.38 (test0.2/0.18; 0.55/0.51) |
| 49 |    BinThrs_2=0.33; %0.33 |
| 50 | |
| 51 | % Inputs for Thresholds |
| 52 |    idxFac=col/256; |
| 53 |    idyFac=row/192; |
| 54 |    sStart =1;sEnd =numSlice; % plot slice(s) of interest |
| 55 |    ckSlice2 =sStart:numSlice; |
| 56 |    xShiftR=25*idyFac;yShiftU=-11*idxFac; % ROI shift from center |
| 57 |    %radi = round(col/5*row/192); % radius of bound ROI |
| 58 |    radi = round(col/5); % radius of bound ROI |
| 59 |    BW_percentThrs = BinThrs_1; % binary (black/white) percent threshold |
| 60 |    removeSmallObjPixel = round(col/13/2*row/192); % defind area size presum as too small |
| 61 |    diskFilter = 3; % filter for fill-in & expand |
| 62 |    cenErrThrs = 13*col/256*row/192; % centroid error threshold (max allow index from center ref) |
| 63 |    areaMin = col/6*row/192; % min area detection require |
| 64 |    areaMax = col*row/40; % max area detection require |
| 65 | |
| 66 | % slices pick ONLY for debug display |
| 67 | if strcmp(fileNameNum,'0556') |
| 68 |    ckSlice =66:74; %(s70/104 for 0556) |
| 69 | elseif strcmp(fileNameNum,'0622') |
| 70 |    ckSlice =18:30; %(s24/40 for 0622) |
| 71 | elseif strcmp(fileNameNum,'0770') |
| 72 |    ckSlice =44:52; %(s48/96 for 0770) |
| 73 | elseif strcmp(fileNameNum,'0779') |
| 74 |    ckSlice =27:35; %(s31/44 for 0779) |
| 75 | elseif strcmp(fileNameNum,'0782') |
| 76 |    ckSlice =34:42; %(s38/68 for 0782) |
| 77 | elseif strcmp(fileNameNum,'0802') |
| 78 |    ckSlice =24:30; %(s27/51 for 0802) |
| 79 | elseif strcmp(fileNameNum,'1031') |
| 80 |    ckSlice =14:21; %(s17/44 for 1031) |
| 81 | elseif strcmp(fileNameNum,'1048') |

-continued

Listing 1

```
82      ckSlice =30:36;%(s34/48 for 1048)
83    elseif strcmp(fileNameNum,'1224')
84      ckSlice =29:36; %(s33/47 for 1224)
85    elseif strcmp(fileNameNum,'1251')
86      ckSlice =46:58; %(s25/112 for 1251)
87    elseif strcmp(fileNameNum,'hgMRI')
88      ckSlice =13:20; %(17s/26 for hgMRI)
89      BinThrs_1=0.55; %0.38
90      BinThrs_2=0.51; %0.33
91    else
92      hSlice = round(numSlice/2);
93      nn=20;
94      ckSlice = max(1,hSlice-nn):min(hSlice+nn,numSlice);
95    end
96    %%% Start
97
98    % Make Wei threshold to improve pancreas tail detection
99    % if known or after 1st pass detection
100   if flagWeiThrsh==1
101     x1=round(155*col/256);y1=1;x2=round(182*col/256);y2=0.7; % magnify tail
102     m=(y2-y1)/(x2-x1);
103     yintercept= y1-m*x1;
104      yy=ones(1,col);
105     yy(x1:x2)=m*(x1:x2)+yintercept;
106     zz=ones(row,1)*yy;
107     %figure;imagesc(zz)
108     BW_Thrsh=BW_percentThrs*zz; %matrix
109   else
110     BW_Thrsh=BW_percentThrs; %scalar
111   end
112
113   xx=col;yy=row;
114   xCenter=xx/2+xShiftR;
115   yCenter=yy/2+yShiftU;
116   mask0=createCirclesMask([yy xx],[xCenter yCenter],radi); % note the image index on x &y
117   maxVal= max(dataIM,[ ]all');
118   % max max after cut ROI
119   [Y,~]=max(dataIM,[ ],3);
120   test=mask0.*Y;
121   maxSmallCir=max(test,[ ]'all');
122   disp(['maxVal= ' num2str(maxVal),', maxCirVal ' num2str(maxSmallCir) ]);
123   % maxVal =590; % fix max value (not valid)
124   % max value avoid border image
125   %   [Y,~]=max(dataIM,[ ],3);
126   %   mask1=zeros(row,col);
127   %   facRow=round(row*0.05);
128   %   facCol=round(col*0.05);
129   %   mask1(facRow:row-facRow,facCol:col-facCol)=1;
130   %   test=mask1.*Y;
131   %   maxVal= max(test,[ ],'all');
132
133   sliceArea =zeros(1,numSlice); % initialize slice Area
134   sliceIndx = 1: numSlice;
135   for slice=sliceIndx
136     f=squeeze(dataIM(:,:,slice)); % step thru each slice of interest
137     if ismember(slice,ckSlice)
138       figure;subplot(3,3,1);
139       imagesc(f),title(['f',fileNameNum,', Slice = ', num2str(slice),'/' num2str(numSlice)]);colormap gray;axis equal;
140       %imagesc(f,[800,1300]),title(['Original Image Slice = ', num2str(slice)]);
141     end
142     f2= f.*mask0;
143     if ismember(slice,ckSlice);subplot(3,3,2);imagesc(f2);title('Image with Bound ROI');colormap gray;axis equal;end
144
145     BW=imbinarize(f2/maxVal,BW_Thrsh); % select BW with thrsh exceed X%
146
147     if ismember(slice,ckSlice);subplot(3,3,3);imagesc(BW);title('Binary Image Threshold');colormap gray;axis equal;end
148     BW2 = bwareaopen(BW, removeSmallObjPixel); % remove small objects
149     if ismember(slice,ckSlice);subplot(3,3,4);imagesc(BW2);title('Remove Small Objects');colormap gray;axis equal;end
150     mask2 = BW2;
151
152     s = regionprops(mask2,'centroid');
153     p = regionprops(mask2,'PixelList');
```

Listing 1

```
154    a = regionprops(mask2,'Area');
155    numBlobs = length(s);
156    if ismember(slice,ckSlice)
157      hold on; % label blob for analysis
158      for ii=1:numBlobs
159        text(s(ii).Centroid(1),s(ii).Centroid(2),num2str(ii),'Color','red')
160      end
161      hold off;
162    end
163
164    for ii=1:numBlobs
165      centroidErr= s(ii).Centroid - [xCenter yCenter];
166      inPan = max(abs(centroidErr))< cenErrThrs;% | | ... % within centroid of the whole pancrea
167      if ¯inPan | | a(ii).Area< areaMin | | a(ii).Area> areaMax % not within Pan or if araea too small or too big
168        x1=p(ii).PixelList(:,2);
169        y1=p(ii).PixelList(:,1);
170        nPix=length(p(ii).PixelList(:,2));
171        %mask2(x1,y1)=0;
172        for jj=1:nPix;mask2(x1(jj),y1(jj))=0;end
173      end
174    end
175    % remove all if mask TOTAl area (for multi blobs)below required area
176    totalArea= sum(mask2,'all');
177     if totalArea< 2*areaMin
178        mask2=zeros(size(mask2));
179    else
180        sliceArea(slice)=totalArea;
181    end
182
183    if ismember(slice,ckSlice);subplot(3,3,5);imagesc(mask2);title('Remove Blobs');colormap gray;axis equal;end
184    %maskSlim(:,:,slice)=mask2;
185
186    mask3 = imdilate(mask2, strel('disk', diskFilter)); % expand mask frame
187    if ismember(slice,ckSlice);subplot(3,3,6);imagesc(mask3);title('Mask Expand(disk)');colormap gray;axis equal;end
188
189    se = strel('disk',15);
190    %mask4 = imclose(mask3, se);
191     mask4 = mask3;
192    if ismember(slice,ckSlice);subplot(3,3,7);imagesc(mask4);title('Mask Fill-in(disk)');colormap gray;axis equal;end
193
194    f3=f.*mask4;
195    if ismember(slice,ckSlice)
196      subplot(3,3,8);
197      imagesc(f3);title('Original Image with Mask');
198      if dataType==2;imagesc(f3,[900 1500]);title('Original Image with Mask');colormap gray;axis equal;end
199    end
200    maskIM(:,:,slice)=mask3;
201    if ismember(slice,ckSlice)
202      subplot(3,3,9);
203      imagesc(f),title('Mask Boundary');colormap gray;axis equal;
204      if max(mask4,[ ],'all')>0
205        hold on;
206        B = bwboundaries(mask4);
207        % plot boundary for each blob
208        for k=1:length(B)
209          bound = B{k};
210          xx=bound(:,2);yy=bound(:,1);
211          plot(xx,yy,'g','LineWidth',0.9);
212        end
213        hold off
214        %contour(mask4;'g')hold off;
215      end
216    end
217    %pause(1)
218  end
219  validSlice1= find(sliceArea>0);
220  if isempty(validSlice1) % no Slice detect
221    disp('Pass 1, No Detection ');
```

Listing 1

```
222    return;
223  else
224    disp(['detect slice Pass 1: ' num2str(validSlice1)]);
225  end
```

Listing 2

```
 1   %% Part2
 2   % Thresholds for 2nd round (~repeat process with lower threshold)
 3   BW_percentThrs = BinThrs_2; % black/white percent threshold (lower to pick up small
     part)
 4   areaMin = col/10*row/192; % min area detection require
 5   areaMax = col*row/35; % max area detection require (allow more)
 6
 7   centerSlice=round(median([find(sliceArea>0.9*max(sliceArea))
     find(sliceArea==max(sliceArea))]));% add in extra to offset even #
 8   disp(['slice center ' num2str(centerSlice)]); % define as center detection
 9   sliceInterest= centerSlice-2:centerSlice+2; %
10   combMask= sum(maskIM(:,:,sliceInterest),3);
11   figure;imagesc(combMask); title ('Combine all Masks from Pass 1');axis equal;
12   % if max(combMask,[ ]'all')==0;disp('Pass2, No Mass ');return;end % stop no mask
13
14   B = bwboundaries(combMask);% boundary of the Pancreas mask
15   boundM= B{1};% boundary of the mask read in
16   hold on;
17   plot(boundM(:,2),boundM(:,1),'r');
18   hold off
19   combMask1= combMask>0; % mask for combine slice about center slice
20   % find pancreas mean across x-axis
21   f=squeeze(dataIM(:,:,centerSlice)); % select slide of interest
22   test =f.*combMask1;
23   meanXaxis = sum(test,1)./sum(test>0,1);
24   figure;plot(meanXaxis); grid on; title ('Pancreas area ave across vertical dim'); % see
     pan
25   test2=smooth(meanXaxis,20);
26
27   %combMaskSlim= sum(maskSlim(:,:,sliceInterest),3);
28   %figure;imagesc(combMaskSlim);
29   %combMaskSlim1= combMaskSlim>0;
30
31   sliceIndx2= centerSlice-3:centerSlice+4; % define as slices of interest about the center
     detection slice
32   sliceArea =zeros(1,numSlice);
33   Xslice =2; % perform 3D sliding correlation about +/- X slices on each side
34   %% start 2nd loop
35   for slice=sliceIndx2
36       % Correlation 3D about +/- Xslice
37       sliceStart= max(sliceIndx2(1),slice-Xslice);
38       sliceEnd= min(sliceIndx2(end),slice+Xslice);
39       sliceInterest= sliceStart:sliceEnd;
40       combMask= sum(maskIM(:,:,sliceInterest),3); % mask for 3D slices correlation
41       combMask1= combMask>0; % make binary mask
42
43       f=squeeze(dataIM(:,:,slice)); % select slide of interest
44       if ismember(slice,ckSlice2)
45          figure;
46          subplot(3,3,1);
47          imagesc(f),title([f',fileNameNum,' P2, Slice = ', num2str(slice),'/',
     num2str(numSlice)]);colormap gray;
48          %imagesc(f,[800,1300]),title(Image Slice = ', num2str(slice)]);
49          hold on;
50          B = bwboundaries(mask0);
51          % plot boundary for mask0
52          for k=1:length(B)
53             bound = B{k};
54             xx=bound(:,2);yy=bound(:,1);
55             plot(xx,yy,'y--','LineWidth',0.9);
56          end
57          hold off
58       end
```

Listing 2

```
59      f2= f.*mask0;
60      if ismember(slice,ckSlice2);subplot(3,3,2);imagesc(f2);title('Image with Bound
        ROI')colormap gray;end
61
62      BW=imbinarize(f2/maxVal,BW_percentThrs); % select BW with thrsh exceed X%
63      if ismember(slice,ckSlice2);subplot(3,3,3);imagesc(BW);title('Binary Image
        Threshold');colormap gray;end
64      BW2 = bwareaopen(BW, removeSmallObjPixel); % remove small objects
65      if ismember(slice,ckSlice2);subplot(3,3,4);imagesc(BW2);title('Remove Small
        Objects');colormap gray;end
66      mask2 = logical(BW2 .* combMask1);
67      if ismember(slice,ckSlice2);subplot(3,3,5);imagesc(mask2);title('3D mask
        overlay');colormap gray;end
68
69      s = regionprops(mask2,'centroid');
70      p = regionprops(mask2,'PixelList');
71      a = regionprops(mask2,'Area');
72      numBlobs = length(s);
73      if ismember(slice,ckSlice)
74         hold on; % label blob for analysis
75         for ii=1:numBlobs
76            text(s(ii).Centroid(1),s(ii).Centroid(2),num2str(ii),'Color','red')
77         end
78         hold off;
79      end
80
81      for ii=1:numBlobs
82         centroidErr= s(ii).Centroid − [xCenter yCenter];
83         %test each blob is within the selected import pancreas mask
84
85         %subCentroid =
86         %combMask(round(s(ii).Centroid(2)),round(s(ii).Centroid(1))); %test for center
        index only
87
88         dd= 2; % index size near about sub centroid test
89         % Subcentroid test: test if all 4 corners are within the 3D sliding mask
90         C1=combMask1(round(s(ii).Centroid(2))+dd,round(s(ii).Centroid(1))+dd);
91         C2=combMask1(round(s(ii).Centroid(2))−dd,round(s(ii).Centroid(1))−dd);
92         C3=combMask1(round(s(ii).Centroid(2))+dd,round(s(ii).Centroid(1))−dd);
93         C4=combMask1(round(s(ii).Centroid(2))−dd,round(s(ii).Centroid(1))+dd);
94         subCentroid = C1 && C2 && C3 && C4; % sub centroid test
95         mainCentroid = max(abs(centroidErr))< cenErrThrs;
96         % Each blob needs to be either within the 3D sliding mask or near the centroid of
        the main pancreas
97         inPan = subCentroid || ... % test if each blob centroid (4 corners)are within the
        the 3D sliding mask
98         mainCentroid; % within centroid of the whole pancreas
99      %   inPan = max(abs(centroidErr))< cenErrThrs;% || ... % within centroid of the
        whole pancreas
100        % Zero out blob mask if If not in Pan or area too small or too big
101        if ~inPan || a(ii).Area< areaMin || a(ii).Area> areaMax % not within Pan or if
        area too small or too big
102           x1=p(ii).PixelList(:,2);
103           y1=p(ii).PixelList(:,1);
104           nPix=length(p(ii).PixelList(:,2));
105           %mask2(x1,y1)=0;
106           for jj=1:nPix;mask2(x1(jj),y1(jj))=0;end
107        end
108     end
109     % remove all if mask TOTAl area (for multi blobs) below required area
110     totalArea= sum(mask2,'all');
111     if totalArea< 2*areaMin
112        mask2=zeros(size(mask2));
113     else
114        sliceArea(slice)=totalArea;
115     end
116
117     if ismember(slice,ckSlice2);subplot(3,3,6);imagesc(mask2);title('Remove
        Blobs');colormap gray;end
118
119     mask3 = imdilate(mask2, strel('disk', diskFilter)); % expand mask frame
120     if ismember(slice,ckSlice2);subplot(3,3,7);imagesc(mask3);title('Mask
        Expand(disk)');colormap gray;end
121
122
123     b = regionprops(mask3,'Area');
124     numBlobs = length(b);
```

-continued

| | Listing 2 |
|---|---|
| 125 | if numBlobs>1% fill in if more than 1 blob |
| 126 | se = strel('disk',15); |
| 127 | mask4 = imclose(mask3, se); |
| 128 | if ismember(slice,ckSlice2);subplot(3,3,8);imagesc(mask4);title('Mask Fill-in(disk)');colormap gray;end |
| 129 | else |
| 130 | mask4 = mask3; |
| 131 | f3=f.*mask4; |
| 132 | if ismember(slice,ckSlice2) |
| 133 | subplot(3,3,8); |
| 134 | imagesc(f3);title('Original Image with Mask'); |
| 135 | if dataType==2;imagesc(f3,[900 1500]);title('Original Image with Mask');colormap gray;end |
| 136 | end |
| 137 | end |
| 138 | maskIM(:,:,slice)=mask4; |
| 139 | if ismember(slice,ckSlice2) |
| 140 | subplot(3,3,9); |
| 141 | imagesc(f),title('Mask Boundary');colormap gray; |
| 142 | if max(mask4,[ ],'all')>0 |
| 143 | hold on; |
| 144 | B = bwboundaries(mask4); |
| 145 | % plot boundary for each blob |
| 146 | for k=1:length(B) |
| 147 | bound = B{k}; |
| 148 | xx=bound(:,2);yy=bound(:,1); |
| 149 | plot(xx,yy,'g','LineWidth',0.9); |
| 150 | end |
| 151 | hold off |
| 152 | %contour(mask4,'g')hold off; |
| 153 | end |
| 154 | end |
| 155 | pause(1) |
| 156 | end |
| 157 | |
| 158 | validSlice2= find(sliceArea>0); |
| 159 | disp(['detect slice Pass 2: ' num2str(validSlice2)]); |
| 160 | |
| 161 | %%% SAVE data |
| 162 | |
| 163 | if saveMaskFlg==1 |
| 164 | if dataType==1 |
| 165 | save ('C:\data\Work\Apollo_MDA\2019\data\highGrade\MRI_PancreasMask','maskIM');' |
| 166 | elseif dataType==2 |
| 167 | save ('C:\data\Work\Apollo_MDA\2019\data\highGrade\CT_AR_PancreasMask','maskIM'); |
| 168 | end |
| 169 | end |
| 170 | %save ('mask2_1043','mask2'); % slice 17/44 |

| | Listing 3 |
|---|---|
| 1 | clear |
| 2 | |
| 3 | frame_num = 0; |
| 4 | |
| 5 | figure |
| 6 | |
| 7 | use_mask = 1; |
| 8 | |
| 9 | load('F:\data\2019-01-28\Pancreatic cyst cases\serial CTs before resection (Low grade IPMN)\lgCT3.mat') |
| 10 | |
| 11 | %load('F:\data\2019-01-28\Pancreatic cyst cases\CT and MRI before resection (high grade IPMN)\CT_AR_PancreasMask.mat') |
| 12 | |
| 13 | %%% |
| 14 | load('D:\Documents\Apollo\fromTuan\2019-Apr-06-MDA-telecon\CT3_LG_AR_PancreasMask.mat') |
| 15 | CT_ARmask = maskIM; |
| 16 | %%% |
| 17 | |
| 18 | % LgCT3AR(LgCT3AR<800)=800; |

| Listing 3 |
| --- |

```
19   % LgCT3AR = 0.05*LgCT3AR;
20
21   LgCT3AR_mask = LgCT3AR.*CT_ARmask;
22
23   if use_mask
24     [~,zmax]= max(max(squeeze(max(LgCT3AR.*CT_ARmask,[ ],1)),[ ],1));
25   end
26
27   maskIdx = find(max(squeeze(max(CT_ARmask,[ ],1)),[ ],1));
28
29   if use_mask
30     idx1 = min(maskIdx);
31     for k = -1 : -1
32       LgCT3AR(:,:,idx1-k) = LgCT3AR(:,:,idx1);
33     end
34     idx2 = max(maskIdx);
35     for k = 1 : 1
36       LgCT3AR(:,:,1dx2+k) = LgCT3AR(:,:,1dx2);
37     end
38     maxMask = max(LgCT3AR(:,:,idx1),LgCT3AR(:,:,1dx2));
39     for z = idx1-1:1dx2+1, LgCT3AR(:,:,z) =maxMask; end end
40
41   im0 = max(LgCT3AR,[ ],3)+mean(LgCT3AR,3)+std(LgCT3AR,[ ],3);
42   image(0.05*im0)
43   colormap(gray(256))
44   truesize
45
46   frame_num =frame_num + 1;
47   Mov(frame_num) = getframe;
48
49   for frame_num = 2 : 30
50     Mov(frame_num) = Mov(1);
51     pause(0.1)
52   end
53
54   im1 = max(LgCT3AR(:,:,zmax-1:zmax+1),[ ],3) + ...
55     mean(LgCT3AR(:,:,zmax-1:zmax+1),3) + ...
56     std(LgCT3AR(:,:,zmax-1:zmax+1),[ ],3);
57
58   %image(im1)
59   %colormap(gray(256))
60
61   for frame_num = 31 : 60
62     wt = (frame_num - 30)/30;
63     im2 = wt*im1 + (1-wt)*im0;
64     image(0.05*im2)
65     Mov(frame_num) = getframe;
66     pause(0.1)
67   end
68
69
70
71   zIdx = zmax + (-1:1);
72
73   r = imsharpen(squeeze(LgCT3AR(:,:,zIdx(1))),'Radius',1,'Amount',4);
74   g = imsharpen(squeeze(LgCT3AR(:,:,zIdx(2))),'Radius',1,'Amount',4);
75   b = imsharpen(squeeze(LgCT3AR(:,:,zIdx(3))),'Radius',1,'Amount',4);
76
77   im3(:,:,1)=imresize(r,1,'bilinear');
78   im3(:,:,2)=imresize(g,1,'bilinear');
79   im3(:,:,3)=imresize(b,1,'bilinear');
80   image(3*im3/1e3-0.5)
81
82   drawnow
83
84   Mov2 = getframe;
85
86
87   for frame_num = 61 : 90
88
89     wt = (frame_num-60)/30;
90
91     image( Mov(60).cdata*(1-wt) + Mov2.cdata*wt )
92
93     drawnow
94
95     Mov(frame_num) = getframe;
```

Listing 3

```
96
97      pause(0.1)
98
99   end
100
101
102
103  for alpha = [0 : 0.02 : 0.3]
104
105     scan = LgCT3AR.*(alpha*CT_ARmask+1-alpha);
106
107     [Nx,Ny,Nz] = size(scan);
108
109
110     if ~use_mask
111        E = zeros(1,Nz);
112
113        for z = 1 : Nz
114
115           temp_in = scan(Nx/2-50:Nx/2+50,Ny/2-45:Ny/2+90,z);
116           temp_in = temp_in(:);
117
118           E(z) = std(temp_in(temp_in>mean(temp_in)));
119
120        end
121
122        %E = conv(E,ones(1,7),'same');
123        E = detrend(E);
124
125        [~,zmax] = max(E);
126     end
127
128
129     zIdx = zmax + (-1:1);
130
131     r = imsharpen(squeeze(scan(:,:,zIdx(1))),'Radius',1,'Amount',4);
132     g = imsharpen(squeeze(scan(:,:,zIdx(2))),'Radius',1,'Amount',4);
133     b = imsharpen(squeeze(scan(:,:,zIdx(3))),'Radius',1,'Amount',4);
134
135     im3(:,:,1)=imresize(r,1,'bilinear');
136     im3(:,:,2)=imresize(g,1,'bilinear');
137     im3(:,:,3)=imresize(b,1,'bilinear');
138     image( 3*1m3/1e6-0.5)
139
140     drawnow
141
142     frame_num = frame_num + 1;
143
144
145     Mov(frame_num) = getframe;
146
147
148
149  end
150
151
152  %movie(Mov,-10,2)
```

Listing 4

```
1   rIdx = k-1;   gIdx = k;   bidx = k+1;
2   r = imsharpen(squeeze(Masked_CT(:,:,rIdx)),'Radius',1,'Amount',4);
3   g = imsharpen(squeeze(Masked_CT(:,:,gIdx)),'Radius',1,'Amount',4);
4   b = imsharpen(squeeze(Masked_CT(:,:,bIdx)),'Radius',1,'Amount',4);
```

Listing 5

```
1   L=4;
2   ridx = (1:L);
3   gidx = ridx + L;
4   bidx = gidx + L;
5
6   R = Masked_CT(:,:,ridx);
7   G = Masked_CT(:,:,gidx);
8   B = Masked_CT(:,:,bidx);
9
10  r = max(R,[ ],3) + mean(R,3) + std(R,[ ],3);
11  g = max(G,[ ],3) + mean(G,3) + std(G,[ ],3);
12  b = max(B,[ ],3) + mean(B,3) + std(B,[ ],3);
13
14  r = imsharpen(r,'Radius',1,'Amount',4);
15  g = imsharpen(g,'Radius',1,'Amount',4);
16  b = imsharpen(b,'Radius',1,'Amount',4);
17
```

-continued

Listing 5

```
18    im3(:,:,1)=r;
19    im3(:,:,2)=g
20    im3(:,:,3)=b;
21
22    image(G*im3)
```

As used herein, the word "or" is inclusive, so that, for example, "A or B" means any one of (i) A, (ii) B, and (iii) A and B. As used herein, when one quantity (e.g., a first array) is referred to as being "based on" another quantity (e.g., a second array) it means that the second quantity influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory) as the second quantity. Although some examples described herein are related to displaying a pancreas, the present disclosure is not limited to such uses and it may be applied to various other organs or features in an object being imaged.

The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example a processing circuit may include two processing circuits, an FPGA and a CPU, interconnected on a PCB.

Although limited embodiments of a system and method for isolating organs in medical imaging scans have been specifically described and illustrated herein, many modifications and variations will be apparent to those skilled in the art. Accordingly, it is to be understood that a system and method for isolating organs in medical imaging scans employed according to principles of this invention may be embodied other than as specifically described herein. The invention is also defined in the following claims, and equivalents thereof.

What is claimed is:

1. A method for displaying scan data, the method comprising:
    forming, from a first scan data array based on raw scan data, a first mask, each element of the first mask being one or zero according to whether the corresponding element of the first scan data array exceeds a first threshold;
    forming, from the first scan data array, a second mask, each element of the second mask having a value of one or zero according to whether the corresponding element of the first scan data array exceeds a second threshold, the second threshold being less than the first threshold;
    forming a fourth mask, the fourth mask being the element-wise product of the second mask and a three dimensional array third mask, the third mask being based on the first mask and a three dimensional array fifth mask, wherein the forming of the third mask comprises forming a slice of the third mask from a plurality of slices of the fifth mask, and wherein the forming of the third mask comprises forming a slice of the third mask from a plurality of slices of the fifth mask, each element of the slice of the third mask having a value of one, when any of the corresponding elements of the plurality of slices of the fifth mask has a value of one; and zero, otherwise;
    storing the first, second, third, fourth and fifth marks in a storage device; and
    displaying an improved scan data on a display device by applying the stored masks to the scan data.

2. The method of claim 1, further comprising forming the sixth mask based on a seventh mask, the seventh mask being based on the first mask, the forming of the sixth mask comprising setting to zero, in the sixth mask, one or more first connected regions,
    each of the first connected regions being an 8-connected region of ones, for which a measure of separation between a centroid of the first connected region and an estimated organ center exceeds a threshold distance.

3. The method of claim 2, wherein the measure of separation is a Chebyshev norm.

4. The method of claim 2, wherein the forming of the sixth mask further comprises setting to zero one or more second connected regions, each of the second connected regions having an area exceeding an upper area threshold.

5. The method of claim 4, wherein the forming of the sixth mask further comprises setting to zero one or more third connected regions, each of the third connected regions having an area less than a lower area threshold.

6. The method of claim 1, further comprising forming the first scan data array by multiplying a second scan data array by a cylindrical mask, the second scan data array being based on the raw scan data, each element of the cylindrical mask having a value of one if it is inside a cylindrical volume and a value of zero otherwise.

7. The method of claim 1, further comprising forming a fifth mask based on the fourth mask, the forming of the fifth mask comprising setting to zero, in the fifth mask, one or more fourth connected regions,
    each of the fourth connected regions being an 8-connected region of ones, for which:
        at least one corner of a square centered on the centroid of the connected region is at a location corresponding to a value of zero in the third mask, and
        a measure of separation between a centroid of the fourth connected region and an estimated organ center exceeds a threshold distance.

8. The method of claim 7, wherein the forming of the fifth mask further comprises setting to zero one or more fifth connected regions, each of the fifth connected regions having an area exceeding an upper area threshold.

9. The method of claim 8, wherein the forming of the fifth mask further comprises setting to zero one or more sixth connected regions, each of the sixth connected regions having an area less than a first lower area threshold.

10. The method of claim 9, wherein the forming of the fifth mask further comprises:
setting all elements of the fifth mask to zero, when a total number of ones in the fifth mask is below a second lower area threshold, and
leaving the fifth mask unchanged, otherwise.

11. The method of claim 10, further comprising forming a ninth mask based on the fifth mask, the forming of the ninth mask comprising dilating a slice of a mask based on the fifth mask.

12. The method of claim 11, further comprising forming a tenth mask based on the ninth mask, the forming of the tenth mask comprising performing morphological closing on a slice of a mask based on the ninth mask.

13. The method of claim 12, further comprising projecting a third scan data array onto a plane to form a first image comprising a plurality of first pixel values at a plurality of pixel locations, the third scan data array being based on the raw scan data, the projecting comprising:
forming a vector for each pixel, the vector corresponding to array elements, of the third scan data array, along a line perpendicular to the plane and passing through the pixel location;
calculating a plurality of statistics for each vector; and
calculating the first pixel value for each vector as a weighted sum of the statistics of the plurality of statistics.

14. The method of claim 13, wherein the plurality of statistics comprises two statistics selected from the group consisting of a vector mean, a vector maximum, and a vector standard deviation.

15. The method of claim 14, further comprising projecting a portion of the third scan data array onto a plane to form a second image comprising a plurality of first pixel values at a plurality of pixel locations, the projecting comprising:
forming a vector for each pixel, the vector corresponding to array elements, of the portion of the third scan data array, along a line perpendicular to the plane and passing through the pixel location;
calculating a plurality of statistics for each vector; and
calculating the first pixel value for each vector as a weighted sum of the statistics of the plurality of statistics,
the portion of the third scan data array being a plurality of consecutive slices of the third scan data array, the plurality of consecutive slices of the third scan data array including a maximum-valued slice,
the maximum-valued slice being a slice containing the maximum value of the element-wise product of the third scan data array and the tenth mask.

16. The method of claim 15, further comprising forming a video comprising a first sequence of images, each of the first sequence of images being a different weighted sum of the first image and the second image.

17. The method of claim 16, further comprising forming a third image having:
a first color component based on a first slice of a set of three slices of the element-wise product of the third scan data array and the tenth mask, the three slices including the maximum-value slice;
a second color component based on a second slice of a set of three slices; and
a third color component based on a third slice of a set of three slices.

18. The method of claim 17, wherein the video further comprises a second sequence of images, each of the second sequence of images being a different weighted sum of the second image and the third image.

19. A system comprising:
a processing circuit, and
a non-transitory memory,
the non-transitory memory storing instructions that, when executed by the processing circuit, cause the processing circuit to:
form, from a first scan data array based on raw scan data, a first mask, each element of the first mask being one or zero according to whether the corresponding element of the first scan data array exceeds a first threshold;
form, from the first scan data array, a second mask, each element of the second mask having a value of one or zero according to whether the corresponding element of the first scan data array exceeds a second threshold, the second threshold being less than the first threshold;
form a fourth mask, the fourth mask being the element-wise product of the second mask and a three dimensional array third mask, the third mask being based on the first mask and a three dimensional array fifth mask, wherein the forming of the third mask comprises forming a slice of the third mask from a plurality of slices of the fifth mask, and wherein the forming of the third mask comprises forming a slice of the third mask from a plurality of slices of the fifth mask, each element of the slice of the third mask having a value of one, when any of the corresponding elements of the plurality of slices of the fifth mask has a value of one; and zero, otherwise;
store the first, second, third, fourth and fifth marks in a storage device; and
display an improved scan data on a display device by applying the stored masks to the scan data.

20. The system of claim 19, wherein the instructions further cause the processing circuit to form the sixth mask based on a seventh mask, the seventh mask being based on the first mask, the forming of the sixth mask comprising setting to zero, in the sixth mask, one or more first connected regions,
each of the first connected regions being an 8-connected region of ones, for which a measure of separation between a centroid of the first connected region and an estimated organ center exceeds a threshold distance.

21. The system of claim 20, wherein the measure of separation is a Chebyshev norm.

22. The system of claim 20, wherein the forming of the sixth mask further comprises setting to zero one or more second connected regions, each of the second connected regions having an area exceeding an upper area threshold.

23. The system of claim 22, wherein the forming of the sixth mask further comprises setting to zero one or more third connected regions, each of the third connected regions having an area less than a lower area threshold.

24. The system of claim 19, wherein the instructions further cause the processing circuit to form a fifth an mask based on the fourth mask, the forming of the fifth mask comprising setting to zero, in the fifth mask, one or more fourth connected regions,
    each of the fourth connected regions being an 8-connected region of ones, for which:
        at least one corner of a square centered on the centroid of the connected region is at a location corresponding to a value of zero in the third mask, and
        a measure of separation between a centroid of the fourth connected region and an estimated organ center exceeds a threshold distance.

25. The system of claim 24, wherein the instructions further cause the processing circuit to form a tenth mask based on the fifth mask, the forming of the tenth mask comprising performing morphological closing on a slice of a mask based on the fifth mask.

26. The system of claim 25, wherein the instructions further cause the processing circuit to project a third scan data array onto a plane to form a first image comprising a plurality of first pixel values at a plurality of pixel locations, the third scan data array being based on the raw scan data, the projecting comprising:
    forming a vector for each pixel, the vector corresponding to array elements, of the third scan data array, along a line perpendicular to the plane and passing through the pixel location;
    calculating a plurality of statistics for each vector; and
    calculating the first pixel value for each vector as a weighted sum of the statistics of the plurality of statistics.

27. A system for generating a view of an interior of an object, the system comprising:
    a scanner for scanning the object;
    a processing circuit; and
    a display,
    the processing circuit being configured to:
        form, from a first scan data array based on raw scan data, a first mask, each element of the first mask being one or zero according to whether the corresponding element of the first scan data array exceeds a first threshold;
        form, from the first scan data array, a second mask, each element of the second mask having a value of one or zero according to whether the corresponding element of the first scan data array exceeds a second threshold, the second threshold being less than the first threshold; and
        form a fourth mask, the fourth mask being the element-wise product of the second mask and a three dimensional array third mask, the third mask being based on the first mask and a three dimensional array fifth mask, wherein the forming of the third mask comprises forming a slice of the third mask from a plurality of slices of the fifth mask, and wherein the forming of the third mask comprises forming a slice of the third mask from a plurality of slices of the fifth mask, each element of the slice of the third mask having a value of one, when any of the corresponding elements of the plurality of slices of the fifth mask has a value of one; and zero, otherwise;
        store the first, second, third, fourth and fifth marks in a storage device; and
        display an improved scan data on a display device by applying the stored masks to the scan data.

28. The system of claim 27, wherein the processing circuit is further configured to form the sixth mask based on a seventh mask, the seventh mask being based on the first mask, the forming of the sixth mask comprising setting to zero, in the sixth mask, one or more first connected regions,
    each of the first connected regions being an 8-connected region of ones, for which a measure of separation between a centroid of the first connected region and an estimated organ center exceeds a threshold distance.

29. The system of claim 28, wherein the measure of separation is a Chebyshev norm.

30. The system of claim 28, wherein the forming of the sixth mask further comprises setting to zero one or more second connected regions, each of the second connected regions having an area exceeding an upper area threshold.

31. The system of claim 30, wherein the forming of the sixth mask further comprises setting to zero one or more third connected regions, each of the third connected regions having an area less than a lower area threshold.

32. The system of claim 27, wherein the processing circuit is further configured to form a fifth mask based on the fourth mask, the forming of the fifth mask comprising setting to zero, in the fifth mask, one or more fourth connected regions,
    each of the fourth connected regions being an 8-connected region of ones, for which:
        at least one corner of a square centered on the centroid of the connected region is at a location corresponding to a value of zero in the third mask, and
        a measure of separation between a centroid of the fourth connected region and an estimated organ center exceeds a threshold distance.

33. The system of claim 32, wherein the processing circuit is further configured to form a tenth mask based on the fifth mask, the forming of the tenth mask comprising performing morphological closing on a slice of a mask based on the fifth mask.

34. The system of claim 33, wherein the processing circuit is further configured to project a third scan data array onto a plane to form a first image comprising a plurality of first pixel values at a plurality of pixel locations, the third scan data array being based on the raw scan data, the projecting comprising:
    forming a vector for each pixel, the vector corresponding to array elements, of the third scan data array, along a line perpendicular to the plane and passing through the pixel location;
    calculating a plurality of statistics for each vector; and
    calculating the first pixel value for each vector as a weighted sum of the statistics of the plurality of statistics.

* * * * *